US00PP18119P2

(12) United States Plant Patent
Jandrew

(10) Patent No.: US PP18,119 P2
(45) Date of Patent: Oct. 9, 2007

(54) ***SCAEVOLA* PLANT NAMED 'BOMY BULE'**

(50) Latin Name: *Scaevola aemula*
Varietal Denomination: Bomy Bule

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/386,557

(22) Filed: Mar. 22, 2006

(51) Int. Cl.
*A01H 5/00* (2006.01)

(52) U.S. Cl. ..... Plt./363

(58) Field of Classification Search ..... Plt./363
See application file for complete search history.

*Primary Examiner*—Kent Bell
(74) *Attorney, Agent, or Firm*—Jondle & Associates, P.C.

(57) ABSTRACT

A *Scaevola* plant particularly distinguished by violet-blue flowers with yellow-white eyes, a mid-season, continuous and an abundant flowering response, medium green foliage with purplish stem ends, a vigorous growth habit with a medium to tall plant habit, a decumbent to trailing plant habit with ascending stem ends, a rounded, bushy and well-branched plant habit and good heat tolerance, is disclosed.

2 Drawing Sheets

Genus and species: *Scaevola aemula.*
Variety denomination: 'Bomy Bule'.

BACKGROUND OF THE NEW PLANT

The present invention comprises a new and distinct cultivar of *Scaevola,* botanically known as *Scaevola aemula* and hereinafter referred to by the cultivar name 'Bomy Bule'. The new cultivar originated from a hybridization made in July 2003 in Gilroy, Calif. The female parent was '180', a proprietary violet-flowered *Scaevola* plant (unpatented), while the male parent was '999', a proprietary violet-flowered *Scaevola* plant (unpatented).

The new cultivar was created in July 2003 in Gilroy, Calif. and has been asexually reproduced repeatedly by vegetative cuttings and tissue culture in Gilroy, Calif. and Hillscheid, Germany over a one and one-half-year period. The plant has also been trialed at Gilroy, Calif. and Hillscheid, Germany. The present invention has been found to retain its distinctive characteristics through successive asexual propagations.

Plant Breeder's Rights for this cultivar have been applied for in Canada on Mar. 29, 2005.

SUMMARY OF THE INVENTION

The following are the most outstanding and distinguishing characteristics of the new cultivar when grown under normal horticultural practices in Gilroy, Calif. and Hillscheid, Germany.

1. Violet-blue flowers with yellow-white eyes;
2. A mid-season, continuous and an abundant flowering response;
3. Medium green foliage with purplish stem ends;
4. A vigorous growth habit with a medium to tall plant habit;
5. A decumbent to trailing plant habit with ascending stem ends;
6. A rounded, bushy and well-branched plant habit; and
7. Good heat tolerance.

DESCRIPTION OF THE PHOTOGRAPHS

This new *Scaevola* plant is illustrated by the accompanying photographs which show overall plant habit including inflorescences, buds and foliage of the plant; the colors shown are as true as can be reasonably obtained by conventional photographic procedures. The photos are of a 26-week-old plant grown in a greenhouse in an early Fall trial setting.

DESCRIPTION OF THE NEW CULTIVAR

Figure 1:
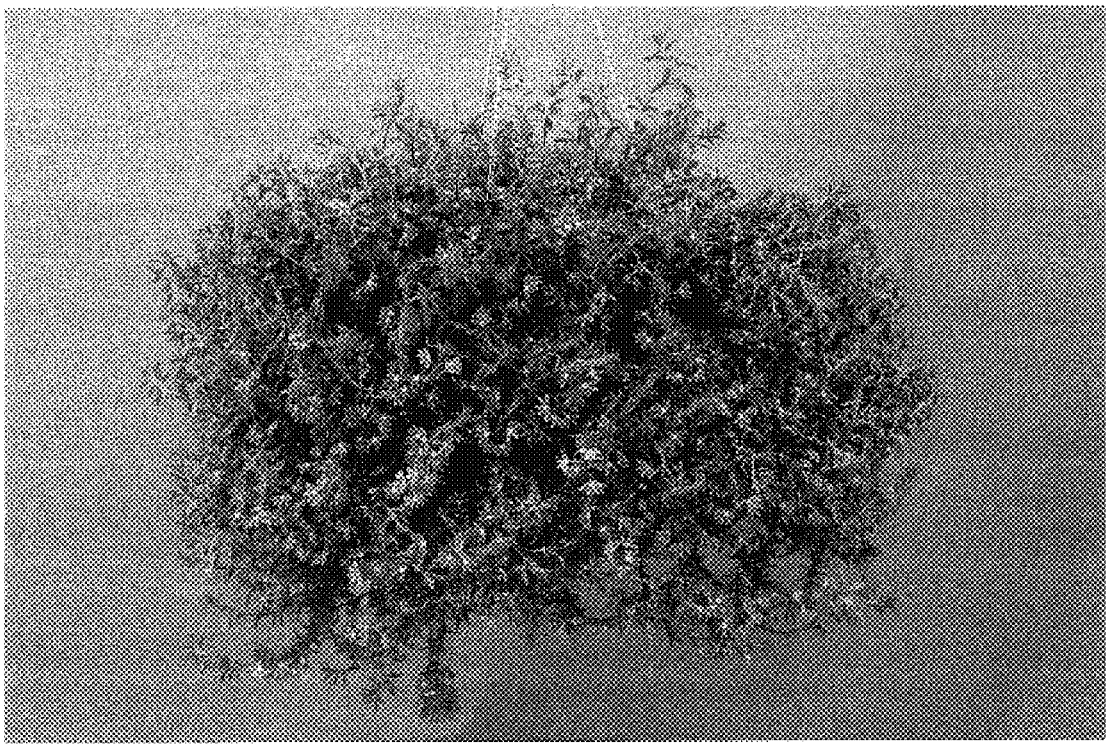
FIG. 1 shows the overall plant habit in a hanging basket, including blooms, buds and foliage.
Figure 2:
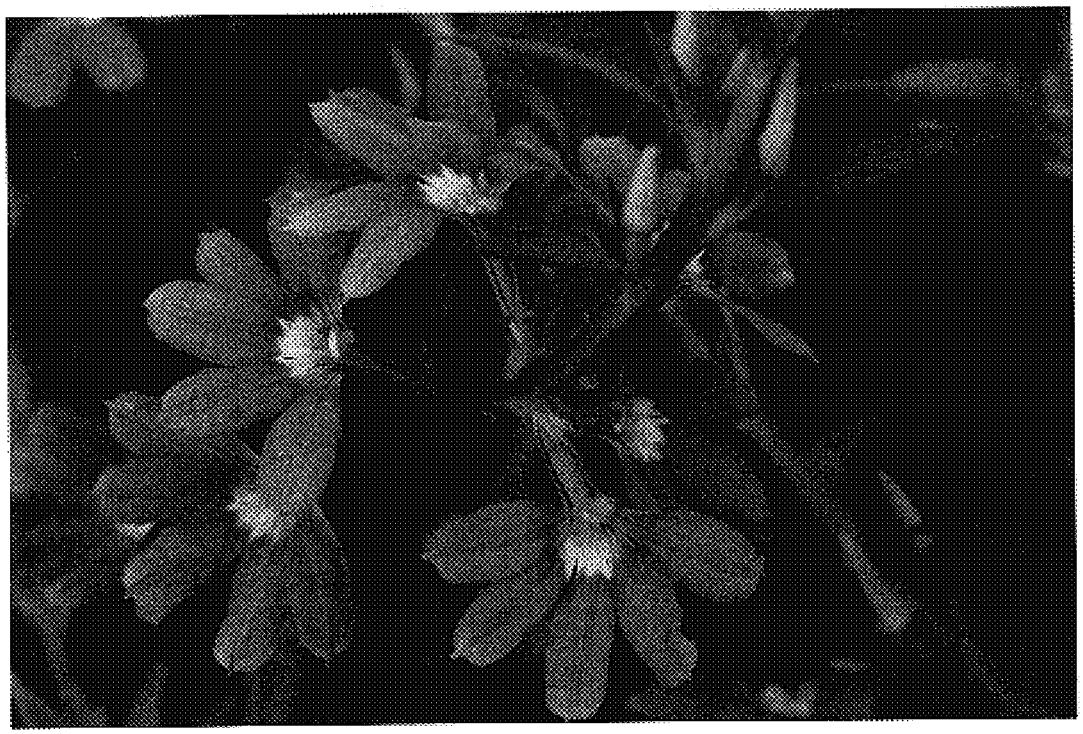
FIG. 2 shows a close-up of the mature inflorescences.

The following detailed descriptions set forth the distinctive characteristics of 'Bomy Bule'. The data which define these characteristics were collected from asexual reproductions carried out in Hillscheid, Germany. Rooted cuttings were planted into 12-cm plastic pots in early March and pinched once. In late May, the plants were transplanted to outdoor hanging baskets that were situated under light rain protection. The plant history was taken on 11-week-old plants grown in a greenhouse and on 26-week-old plants grown outdoors in Hillscheid, Germany in Summer 2005. Observations were made in early September 2005 when the plants had reached their maximum size. Color readings were taken under natural light. Color references are primarily to The R.H.S. Colour Chart of The Royal Horticultural Society of London (R.H.S.) (2001 edition).

DETAILED BOTANICAL DESCRIPTION

Classification:
*Family*—Goodeniaceae.
*Botanical.*—*Scaevola aemula.*
*Common name.*—Fan flower.

Parentage:
*Female parent.*—'180', a proprietary (unpatented) violet-flowered *Scaevola* plant.

*Male parent.*—'999', a proprietary (unpatented) violet-flowered *Scaevola* plant.

Growth:

*Form.*—Herbaceous perennial.

*Growth and branching habit.*—Decumbent to trailing with ascending stem ends.

*Height* (*measured from the top of the soil*).—8.5 cm for an 11-week-old plant.

*Width* (*horizontal plant diameter*).—30 cm for an 11-week-old plant.

*Plant spread* (*from the base to the stem tips, including the flowers*).—85 cm for a mature plant.

*Time to produce a finished flowering plant.*—12 to 14 weeks for a 12-cm pot in the Spring.

*Outdoor plant performance.*—Use in containers and hanging baskets.

*Time to initiate and develop roots.*—About 25 days.

*Root description.*—Fibrous and self-branching.

Stems:

*Number of branches per plant.*—12 to 14.

*Length.*—19 cm for a 10-week-old plant.

*Diameter* (*measured from the midpoint).*—0.3 cm.

*Internode length.*—Up to 6.0 cm for vegetative branches.

*Color.*—RHS 137A (green) for the main part; RHS 177A to RHS 183C (purple-brown) anthocyanin towards the tips.

*Texture.*—Glabrous.

Leaves:

*Arrangement.*—Alternate; the smaller leaves on the flowering stems are roughly at right angles to each other.

*Immature leaf.*—Color: Upper surface: RHS 137B (green) and immature leaves are infused with RHS 183C anthocyanin at the tips. Lower surface: RHS 137C.

*Mature leaf.*—Color: Upper surface: RHS 137B (green). Lower surface: RHS 137C. Length: Up to 7.0 cm on non-flowering plants; later at the flowering stage, 3.5 cm to 4.5 cm at the basal part of the stems and about 1.8 cm at the upper part of the flowering stems. Width: Initially 1.4 cm; at the flowering stage, about 0.9 cm at the lower part of the stems (the non-flowering part) and 0.4 cm for the upper (flowering) part of the stems. Shape: Oblanceolate or spatulate and distinctly dentate for vegetative stems; lanceolate with no to weak dentation and somewhat fleshy for flowering stems. Apex: Obtuse to acute. Base: Attenuate to acute. Margin: Distinctly dentate on non-flowering stems and no to weak dentation for flowering stems. Texture: Leathery; upper surface is pilose and the smaller leaves are somewhat fleshy. Venation: Midrib is longitudinal and protrudes on the lower surface; smaller veins are indistinct. Venation color: RHS 143A for the lower surface; the upper surface is indistinct.

*Petioles.*—Not clearly distinct from the base of the leaf.

Flower buds:

*Shape.*—Elongated and weakly conical.

*Length.*—1.9 cm.

*Diameter.*—0.3 cm to 0.4 cm.

*Color* (*at tight bud*).—RHS N77C (dull purple) with RHS 145A (light green) tips.

Inflorescence:

*Blooming habit.*—Continuously from the Spring through the Fall; flowers appear about 12-weeks after planting rooted cuttings.

*Lastingness of individual blooms on the plant.*—6 to 8 days.

*Fragrance.*—None.

*Inflorescence type.*—Solitary flowers arise from the leaf axils with one flower per leaf axil; indeterminate with 10 to 12 flowers open at any time per stem/branch.

*Flower type.*—Composed of 5 petals fused at the base and in a semicircular or fan-like arrangement to form a lower part which is open tube-shaped; the petals are situated at obtuse angles to the flower base and minimally overlap.

*Pedicels.*—None, flowers are sessile.

Flowers:

*Flower diameter.*—3.0 cm.

*Flower depth.*—2.7 cm.

*Flower tube.*—Shape: Open tube. Tube length: 1.3 cm. Tube diameter (at the opening): 0.4 cm.

*Petals.*—Shape: Roughly elliptical with pointed tips. Apex: Cuspidate. Base: Fused. Margin: Entire. Texture: Smooth, glabrous. Color: Immature: Upper surface: RHS 90B. Lower surface: RHS 91A or slightly deeper. Mature: Upper surface: RHS 92A (bluish-violet) with an RHS N80B (purple-violet) stripe in the middle of the petal with small RHS 8A (yellow-white) eyes. Lower surface: RHS 91A with RHS N155A (whitish) stripes.

*Throat color.*—Inside surface: RHS 151B (greenish-yellow) and RHS 165A (brown) stripes along the edges. Outer surface: RHS 151B (greenish-yellow) and RHS 165A (brown) stripes along the edges.

*Sepals.*—General: Composed of one larger and somewhat fleshy sepal and two narrow sepals at the base of the flower. Shape: Lanceolate for the larger sepal and ligulate for the narrow sepals. Apex: Narrowly acute, pointed. Base: Sessile. Margin: Entire. Texture: Sparsely pubescent. Color: RHS 137A (deep green) for both the upper and lower surfaces. Length: 0.9 cm. Width: 0.1 cm to 0.2 cm.

Reproductive organs:

*Stamen.*—Quantity: 5, protruding from the flower throat. Anther shape: Narrow, ovate. Anther length: 0.2 cm to 0.3 cm. Filament color: RHS 151A (yellowish). Filament diameter: 0.1 cm. Filament length: 0.3 cm. Pollen amount: Sparse. Pollen color: RHS 4D (whitish-yellow).

*Pistil.*—Quantity: 1. Pistil length: 1.5 cm. Style diameter: Up to 0.4 cm at the upper end. Style color: RHS 183B. Stigma color: RHS N155A (whitish with purple hair).

Fruit/seed set: None observed.

Disease and insect resistance: No special observations made.

COMPARISON WITH PARENTAL AND COMMERCIAL CULTIVARS

'Bomy Bule' differs from the female parent '180' (unpatented) in that 'Bomy Bule' has lighter colored flowers, broader leaves and a more compact plant habit than '180'.

'Bomy Bule' differs from the male parent '999' (unpatented) in that 'Bomy Bule' has deeper violet flowers and has an earlier flowering response than '999'. Additionally, 'Bomy Bule' has a more compact plant habit than '999'.

'Bomy Bule' differs from the commercial variety 'Fancy' (U.S. Plant Pat. No. 9,867) in that 'Bomy Bule' has longer stems and longer and more narrow leaves that are directed at almost right angles to the stem, while 'Fancy' has shorter, spoon-shaped leaves that partly cover the stem in an overlapping arrangement. Additionally, the flowering stems of 'Bomy Bule' are longer with a looser arrangement of flowers, while the flowers of 'Fancy' have a tighter arrangement and are closer to the ends of the flowering stems.

'Bomy Bule' differs from the commercial variety 'Newon' (U.S. Plant Pat. No. 10,584), in that 'Bomy Bule' has narrower and more serrated leaves than 'Newon'. Additionally, 'Bomy Bule' has more basal branching than 'Newon'.

I claim:

1. A new and distinct cultivar of *Scaevola* plant as shown and described herein.

* * * * *